United States Patent [19]

Komoto

[11] 4,069,273
[45] Jan. 17, 1978

[54] DIMERIZATION OF LINEAR ALPHA-OLEFINS

[75] Inventor: Robert G. Komoto, Emeryville, Calif.

[73] Assignee: Chevron Research Company, San Francisco, Calif.

[21] Appl. No.: 761,916

[22] Filed: Jan. 24, 1977

[51] Int. Cl.$^2$ ................................................ C07C 3/10
[52] U.S. Cl. ........................................... 260/683.15 D
[58] Field of Search .............................. 260/683.15 D

[56] References Cited

U.S. PATENT DOCUMENTS

| | | | |
|---|---|---|---|
| 3,736,264 | 5/1973 | Chauvim | 260/683.15 D |
| 4,020,121 | 4/1977 | Kister et al. | 260/683.15 D |

*Primary Examiner*—C. Davis
*Attorney, Agent, or Firm*—D. A. Newell; John Stoner, Jr.; W. Keith Turner

[57] ABSTRACT

Linear alpha-olefins are dimerized using a process which comprises contacting a low-molecular-weight linear alpha-olefin with a catalyst system comprising a zero-valent nickel compound and hexafluoro-2,4-pentanedione.

4 Claims, No Drawings

DIMERIZATION OF LINEAR ALPHA-OLEFINS

BACKGROUND OF THE INVENTION

This invention concerns a process for producing high-molecular weight linear alpha-olefins by catalytic dimerization of low molecular weight linear alpha-olefins. In particular, the process uses a catalyst prepared by complexing bis(1,5-cyclooctadiene) nickel(0) and hexafluoro-2,4-pentanedione. The product olefins, particularly the intermediate weight range olefins, are used to prepare biodegradable detergents. For instance, such olefins can be reacted with sulfur trioxide to prepare alpha-olefin sulfonates. Alternatively, the olefins can be converted to the corresponding alcohol using the "oxo" process or sulfuric acid catalyzed hydration. The alcohol can be ethoxylated with ethylene oxide to form conventional detergent compounds.

A variety of catalysts have been proposed for use in dimerization or oligomerization processes. U.S. Pat. No. 3,676,523, granted July 11, 1972, discloses ethylene growth catalysts prepared using divalent nickel salts, a reducing agent and an o-dihydrocarbylphosphinobenzoate ligand. U.S. Pat. No. 3,825,615, granted July 23, 1974, discloses catalysts prepared using divalent nickel salts, a reducing agent and dicyclohexylphosphinopropionic acid or a salt thereof.

Catalysts comprising zero-valent nickel compounds have also been used in ethylene oligomerization processes. For instance, U.S. Pat. No. 3,644,563 discloses a process for oligimerizing ethylene which employs a catalyst comprising a nickel chelate of a bidentate ligand having a tertiary organophosphorus moiety and a carboxymethyl or carboxyethyl group attached directly to the phosphorus atom of the organophosphorus moiety and an inorganic siliceous oxide support. U.S. Pat. No. 3,644,564 discloses an ethylene oligomerization process using a catalyst which is the product of the reaction of a nickel compound which is an atom of nickel in complex with an olefinically unsaturated compound with a fluorine-containing ligand. The preferred nickel compound is bis(1,5-cyclooctadiene) nickel(0). The fluorine-containing ligands are selected from the group consisting of trifluoroacetic acid, 4,4,4-trifluoro-3-hydroxy-3-trifluoromethylbutyric acid, perfluoropropene, hexafluoro, acetylacetone and trifluoroacetylacetone. Catalyst systems for dimerizing 1-olefins have also been suggested in the art. For instance, J. R. Jones, Journal of Chemical Society (C), 1124 (1971) discusses the dimerization of propene and other 1-olefins with a homogenous catalyst system comprising nickel acetylacetonate and diethylaluminum ethoxide.

Previously known processes which concern alpha-olefin dimerization, generally, produce a large proportion of polymer and a relatively small proportion of dimer. For instance, U.S. Pat. No. 3,825,615 describes the molecular weight distribution of typical products as conforming to a geometric distribution pattern expressed by the mathematical equation.

$$K = (C_{n+2})/(C_n) \text{ (mols.)}$$

That is, over the entire range of oligomers produced, the mol ratio of a given oligomer, $C_{n+2}$, over the one directly preceding it, $C_n$, remains essentially constant. In order to obtain attractive yields of detergent-range olefins, many processes attempt to control the ratio at about 0.9. This means that the amount of trimer produced according to typical oligomerization processes will approximate the amount of dimer. Where ethylene is the feed monomer, such a ratio is satisfactory. However, where propylene, hexene-1, or other alpha-olefins, besides ethylene, are used as feed olefins, it is especially advantageous to provide a process which produces substantial amounts of intermediate-weight-range dimer.

Moreover, it is important to produce "linear" alpha-olefins. The lineary of the product olefins is especially important where the product is intended for use in detergent manufacture. Thus, it is desirable to provide a catalyst system which not only provides an alpha-olefin dimer, but also provides a linear dimer.

SUMMARY OF THE INVENTION

It has been found that low molecular weight linear alpha-olefins can be dimerized, to prepare a linear dimer, using a catalyst prepared by complexing bis(1,5-cyclooctadiene) nickel(0) and hexafluoro-2,4-pentanedione. The process provides a highly linear alpha-olefin product rich in dimer.

DETAILED DESCRIPTION OF THE INVENTION

Low-molecular-weight linear alpha-olefins which are dimerized by the present catalytic process include, for example, the $C_2$ to $C_8$ linear alpha-olefins and mixtures of these olefins. The $C_3$ to $C_6$ alpha-olefins and their mixtures are particularly preferred.

The catalyst system used in this process comprises a complex of bis(1,5-cyclooctadiene) nickel(0) and hexafluoro-2,4-pentanedione.

Bis(1,5-cyclooctadiene) nickel(0) is described by the structural formula

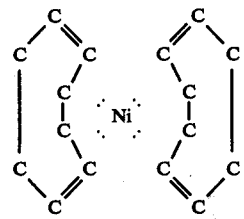

It can be prepared using conventional methods. For example, it has been prepared from nickel diacetylacetonate, ethoxy diethylaluminum, and 1,5-cyclooctadiene by the method described in Inorganic Synthesis 15, 5 (1974).

Hexafluoro-2,4-pentanedione used in the catalyst system is described by the structural formula

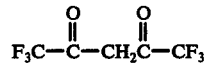

The compound is commercially available or can be prepared by conventional methods. For example, it has been prepared by contacting ethyl trifluoroacetate, 1,1,1-trifluoroacetone, and sodium ethoxide, according to the method described in The Journal of the American Chemical Society, Vol 69, page 1819 (1947).

When preparing the catalyst, the mol ratio of hexafluoropentanedione ligand to nickel should be at least 0.5:1, preferably 1:1. For efficiency and economy, the preferred mol ratio is no greater than 2:1.

The nickel compound used as a catalyst in the present process has been described as comprising a complex of bis(1,5-cyclooctadiene) nickel(0) and hexafluoro-2,4-pentanedione. While this description is suitable for most purposes, it appears likely that the catalyst molecule undergoes chemical transformations during the course of dimerization, possibly involving coordination and/or bonding of olefin to the nickel moiety. In any event, it appears likely that the hexafluoro ligand remains complexed or in some way chemically bonded to the nickel moiety during the course of the reaction and that this complex of nickel and hexafluoro ligand is the effective catalytic species of the dimerization process.

The complex catalyst of this invention is typically formed in situ by contacting the nickel compound and the hexafluoro compound, preferably in an inert diluent or solvent such as toluene or benzene, in the reaction medium. While it is preferred that the catalyst be prepared in the reaction medium, the present invention also encompasses preparing the nickel catalyst prior to its use as a dimerization catalyst. The catalyst preparation is carried out at a temperature from 40° C to about 100° C and contact times from about 30 minutes to about 1 hour.

The nickel catalyst can be used as such or may be employed on an inorganic, solid carrier which remains solid under the reaction conditions. For example, suitable inorganic, solic catalyst carriers include inorganic acidic oxides such as alumina and inorganic materials known as refractory oxides. Suitable refractory oxides include synthetic components as well as acid-treated clays and similar materials. The concentration of the catalyst system should range from about 0.5 molar to about 0.001 molar. However, concentrations ranging from about 0.1 molar to about about 0.01 molar are preferred.

The precise method of establishing olefin/catalyst contact is not critical. In a typical modification, the catalyst composition and the diluent are charged to an autoclave or similar pressure reactor, the olefin feed is introduced, and the reaction mixture is maintained with agitation at reaction temperatures and pressures for the desired reaction. The dimerization is carried out at a temperature from about 50° C to about 100° C, preferably from about 80° C to about 100° C. Where the olefin feed is a gas, the dimerization is carried out at a pressure from about 50 to about 100 psi, preferably from about 80 to about 100 psi, of the feed gas. Where the feed is liquid, the catalyst system can be introduced directly to the feed.

The product, comprising unreacted monomer and dimer, is separated by conventional methods. Unreacted monomer and catalyst can be recycled. The recovered product, primarily linear alpha-olefin dimer, should be separated from the catalyst as soon as possible to avoid continued reaction. Accordingly, continuous operation is advantageous, though batch methods can be used.

EXAMPLE

The following example is intended to further illustrate the invention and should not be construed as limiting its scope.

Dimerization of 1-Hexene 1.0 mmol of bis (1,5-cyclooctadiene) nickel(0), 5 ml of 1-hexene, 10 ml of toluene, 1 ml of n-decane and 1 mmol of hexafluoroacetylacetone were added to an 18-ml stainless steel microbomb. The microbomb was closed and heated to 100° C for 1 hour. Gas chromatographic analysis, after reduction of the olefinic mixture with 100 psi of $H_2$/platinum on carbon, showed 8.5% conversion of 1-hexene to higher olefinic products. A 98% yield of dodecenes having 80% linearity and a 2% yield of octadecenes having 77% linearity were obtained.

When the above procedure was carried out using other ligands, such as acetylacetone, diphenylphosphine, 2,6-dimethylphenylisocyanide/trifluoroacetic acid, dihydrophenanthrene-9,10-dione, 2-(2',6'-dimethylphenylimino)pentane-4-one, triphenylphosphine/2-methylhexanoic acid, and 2-hydroxymethyl pyridine, essentially no conversion of olefin was obtained.

What is claimed is:

1. A process for dimerizing low-molecular-weight linear alpha-olefins which comprises contacting a $C_2$ to $C_8$ linear alpha-olefin or mixture of such olefins with a catalyst prepared by the reaction of bis(1,5-cyclooctadiene) nickel(0) and hexafluoro-2,4-pentanedione, wherein the mol ratio of hexafluoropentanedione to nickel is from about 0.5:1 to about 2:1.

2. A process according to claim 1 in which the nickel salt and hexafluoropentanedione are contacted in the presence of the olefin feed.

3. A process according to claim 1 in which the alpha-olefin feed comprises hexene-1.

4. A process for dimerizing nexene-1 in the liquid phase which comprises contacting hexene-1 with a catalyst prepared by complexing bis(1,5-cyclooctadiend) nickel(0) and hexafluoro-2,4-pentanedione, in the presence of a toluene solvent, wherein the mol ratio of hexafluoropentanedione to nickel is about 1:1.

* * * * *